(12) United States Patent
Rao

(10) Patent No.: US 8,289,031 B1
(45) Date of Patent: Oct. 16, 2012

(54) APPARATUS FOR MEASURING INSULATION CHARACTERISTICS OF COATED STEEL SHEET

(76) Inventor: Dantam K. Rao, Schenectady, NY (US)

( * ) Notice: Subject to any disclaimer, the term of this patent is extended or adjusted under 35 U.S.C. 154(b) by 0 days.

(21) Appl. No.: 13/108,142

(22) Filed: May 16, 2011

(51) Int. Cl.
*H01H 31/12* (2006.01)
*G01R 31/02* (2006.01)

(52) U.S. Cl. .......................... 324/551; 324/541; 324/544

(58) Field of Classification Search .................. 324/509, 324/525, 541, 544, 548, 551, 557; 250/559.4–559.45
See application file for complete search history.

(56) References Cited

U.S. PATENT DOCUMENTS

| | | | | |
|---|---|---|---|---|
| 4,267,506 A * | 5/1981 | Shiell | | 324/755.11 |
| 4,968,947 A * | 11/1990 | Thorn | | 324/701 |
| 5,172,063 A * | 12/1992 | Munikoti et al. | | 324/537 |
| 5,225,785 A * | 7/1993 | Mayer et al. | | 324/671 |
| 5,457,390 A * | 10/1995 | Peterson et al. | | 324/541 |
| 5,867,029 A * | 2/1999 | Iijima et al. | | 324/546 |
| 6,181,139 B1 * | 1/2001 | Joergensen et al. | | 324/455 |
| 6,184,691 B1 * | 2/2001 | Prough | | 324/551 |
| 6,563,334 B2 * | 5/2003 | Tsuru | | 324/762.01 |
| 6,664,794 B1 * | 12/2003 | Fieselman et al. | | 324/525 |
| 6,707,055 B2 * | 3/2004 | Vargas | | 250/559.4 |
| 6,720,790 B2 * | 4/2004 | Eriguchi et al. | | 324/762.01 |
| 7,688,076 B2 * | 3/2010 | Aihara et al. | | 324/522 |
| 7,921,734 B2 * | 4/2011 | Foss et al. | | 73/861.12 |

* cited by examiner

*Primary Examiner* — Huy Q Phan
*Assistant Examiner* — Joshua Benitez Rosario

(57) ABSTRACT

An insulation tester for measuring the surface resistivity of a coated electrical steel sheet using a cylindrical electrode that tests the entire surface area of the sheet. A specific voltage is applied across the insulative coating of the electrical steel sheet using the rotatable cylindrical electrode. The cylindrical electrode is roved over the entire surface of the coated electrical steel sheet to detect insulation defects. This roving tester can be used to locate insulation defects in the coating that can cause core failures, or measure the surface resistivity or dielectric strength of the insulative coating. This tester improves over a conventional Franklin tester which uses discrete button electrodes to test only a small portion of the sheet.

2 Claims, 6 Drawing Sheets

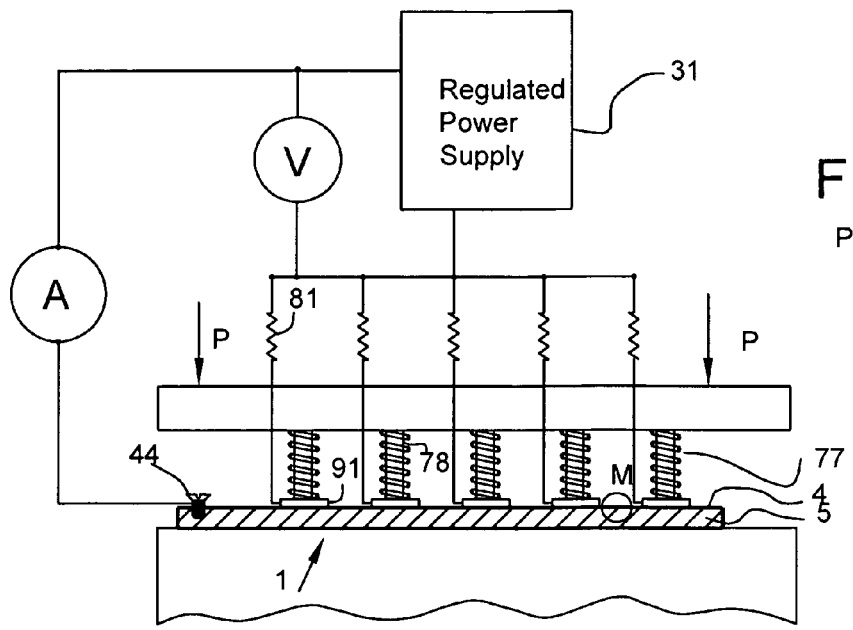
Fig. 1
Prior Art
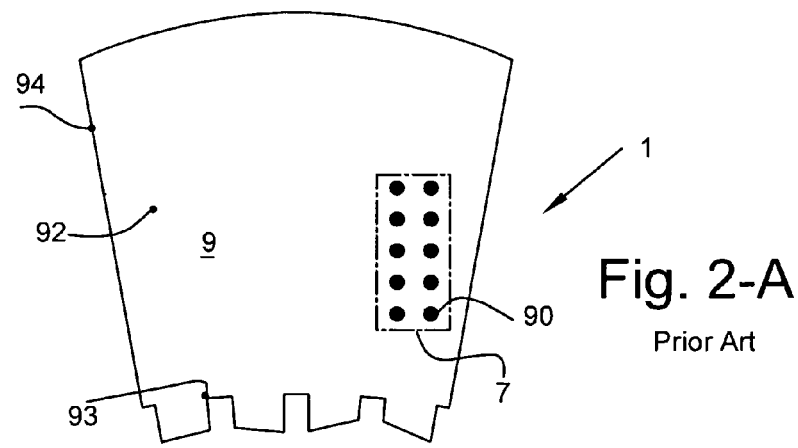
Fig. 2-A
Prior Art
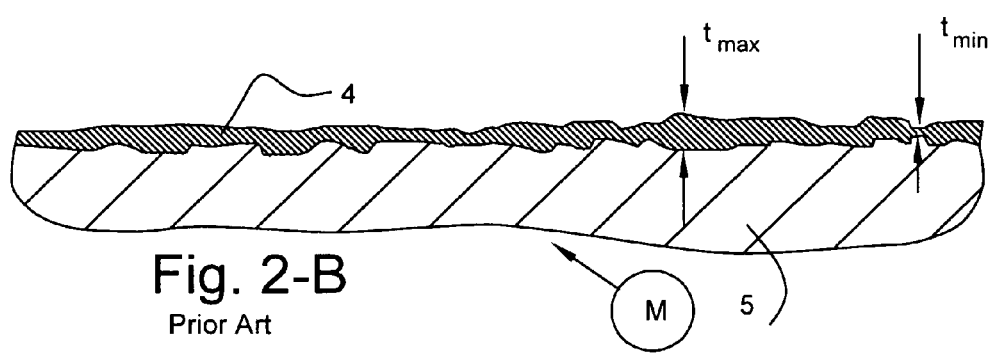
Fig. 2-B
Prior Art

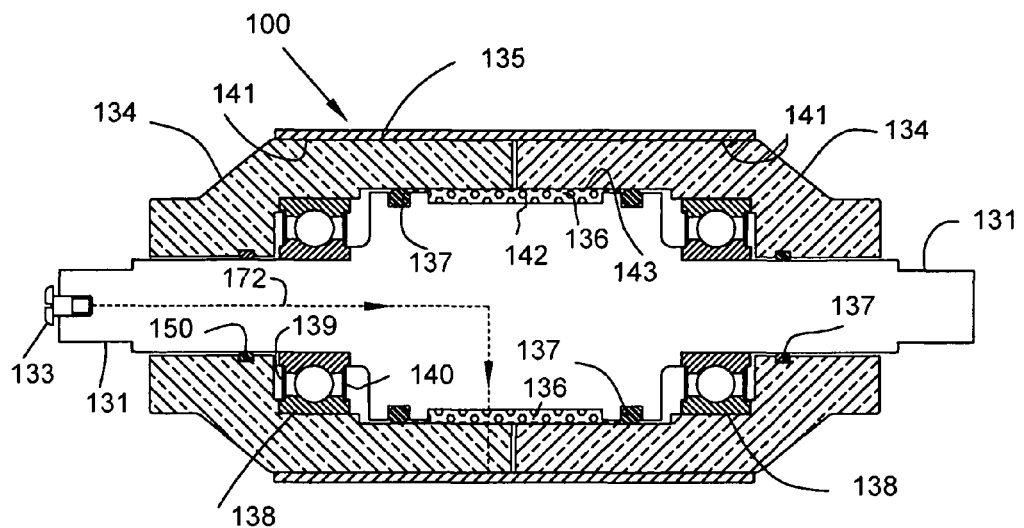
Fig. 3
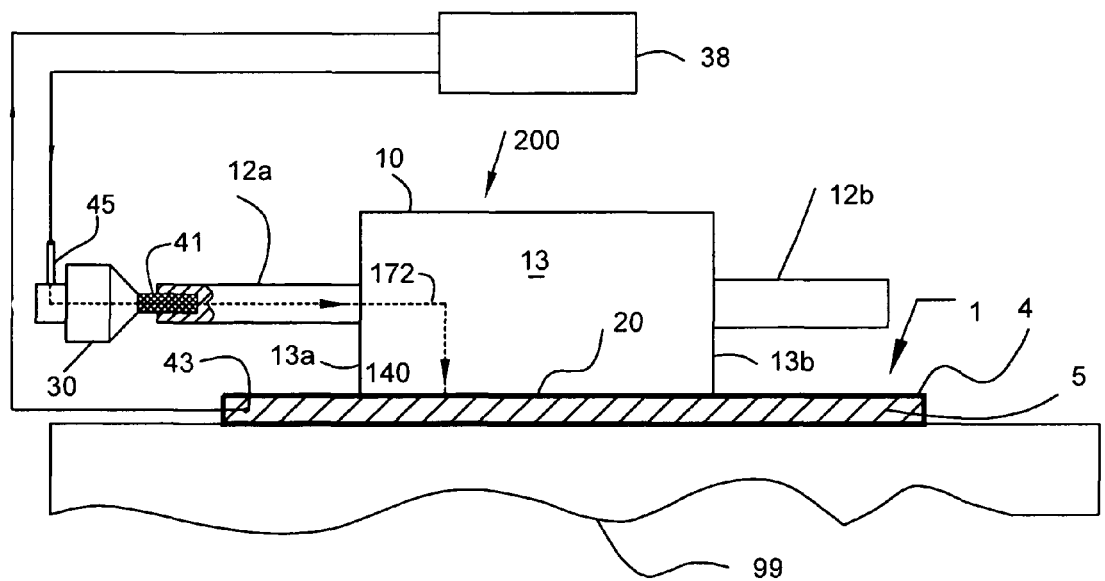
Fig. 4-A

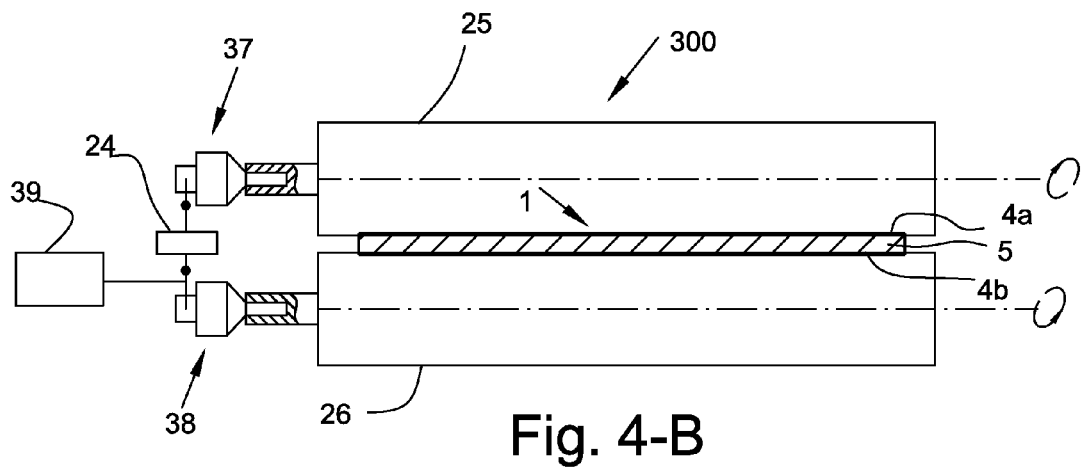
Fig. 4-B
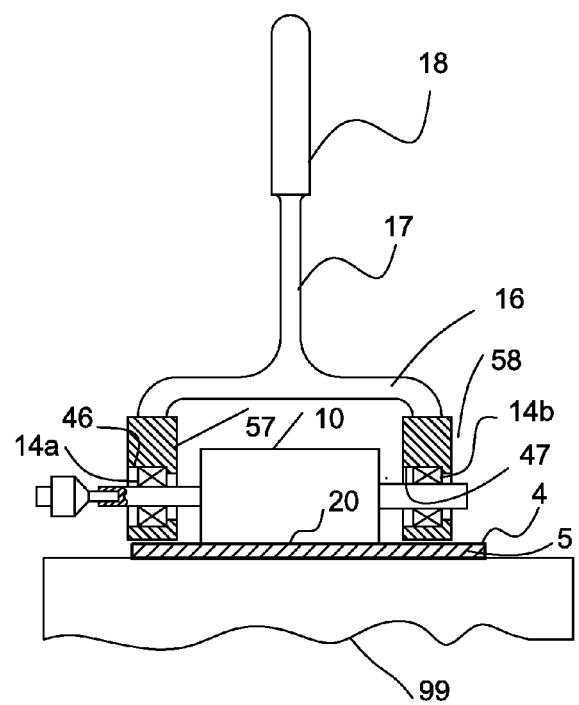
Fig. 5

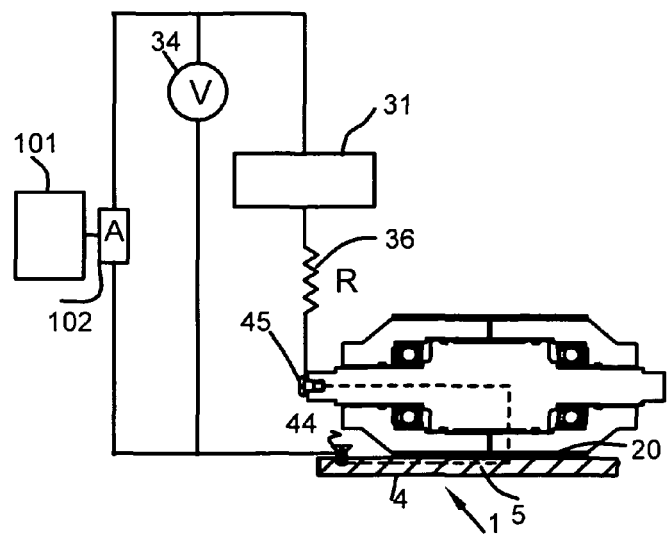
Fig. 8-A
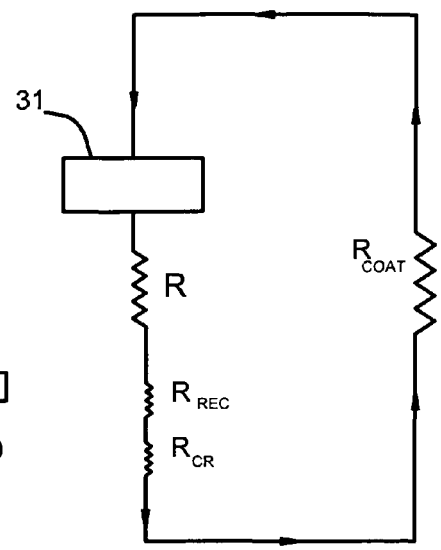
Fig. 8-B
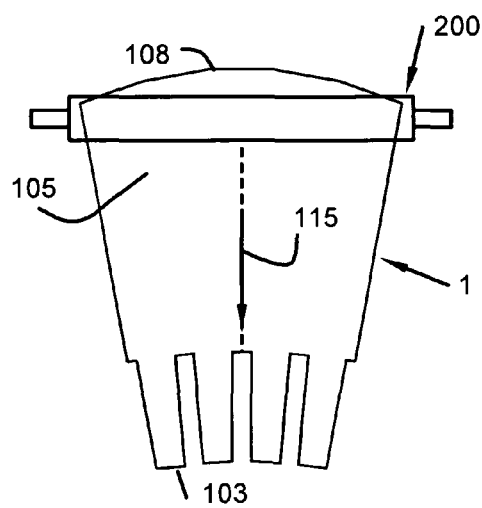
Fig. 9

APPARATUS FOR MEASURING INSULATION CHARACTERISTICS OF COATED STEEL SHEET

FIELD OF THE INVENTION

This invention relates to testing the insulation characteristics of coated surfaces, and specifically to test the coated surface of electrical steel sheets used in electrical machinery.

BACKGROUND OF THE INVENTION

Almost all electrical machines—motors, generators or transformers—use electrical steel to make a stack of laminations. Electrical steel is a thin steel strip with high magnetic permeability. Nominal thickness of coating can range from 0.8 to 8 μm (30 to 300 μinch) and is so thin (akin to surface roughness) that it is generally insulative below a certain voltage and resistive above that voltage, and hence sometimes it is also called a semiconductive coating. Electrical machinery makers punch and shape the steel strip into thin sheets called a lamination, recoat them if needed to improve the insulation quality, and stack them to make the core of an electrical machine. It is well known that a major purpose of insulative coating is to prevent flow of eddy currents from one lamination to next, as excessive eddy currents could cause overheating. The quality of insulation on the coated surface is characterized by surface insulation resistivity (abbreviated as surface resistivity herein). It is the resistance of a unit area of coating, i.e., product of volume resistivity and thickness of the coating. The rationale is that if the surface resistivity is sufficiently high, then the eddy currents that are generated will be relatively small, thereby preventing overheating. With this in mind, a standard test apparatus, termed Franklin tester (see ASTM standard A717-06), was developed to measure the surface resistivity of a single lamination or steel sheet. FIG. 1 and FIG. 2-A show the prior art of testing the insulation characteristics of coated surfaces of electrical steel sheet.

FIG. 1 shows a schematic of the Franklin tester, which comprises a test head and a test head power supply. The test head applies a specified pressure P on the test specimen 1 using two parallel rows of five vertically mounted steel rods 78 free to move axially against surrounding springs 77. Test specimen 1 comprises base metal 5 covered by a thin insulative coating 4 and can be an electrical steel sheet or a lamination. Metallic button electrodes 91 are mounted on each rod 78, and are insulated from the rod. Button electrodes 91 contact the insulated surface 4 at ten discreate areas; they press against the insulated surface 4 defining an imprint 90 of button electrodes on the insulated surface 4 as shown in FIG. 2-A. A power supply 31 applies a potential of 0.5 volt between the electrodes 91 and the test specimen's base metal using a 5 ohm resistor 81 connected in series to each button. A fully conductive sheet yields a "Franklin current" of 1 ampere while a perfectly insulated sheet yields 0 amp. Thus Franklin current ranges between 0 and 1 Amp and indicates the quality of insulation of the coated surface. A simple formula is used to convert the Franklin current into surface resistivity.

Franklin tester is the defacto standard that is used by steel mills and electrical machinery manufacturers to measure the insulation quality of the coating on electrical steel or laminations. But several instances have been reported where Franklin current, measured by a steel mill's Franklin tester, is acceptable, but when measured by an electric machinery maker's Franklin Tester, is unacceptable. Poor repeatability and reproducibility of its results have cast doubts on its usefulness in measuring the insulation quality of electrical steels per Godec (1982).

The prior art has attributed this non repeatability to unequal contact areas of the ten discrete button electrodes; this is believed to be caused by faulty alignment of the ten electrodes, unequal contact pressures exerted on ten different electrodes resulting in uneven wear etc. One of the earliest attempt to achieve repeatability is for an operator to place a fine sandpaper between the ten electrode buttons and a flat plate while under pressure and then remove the sandpaper, thereby polishing the surface of all electrodes. Another method proposed in 1979 in U.S. Pat. No. 4,156,841 is to provide a pivoted tip to the contact electrodes so as to maximize the contact area. Another method proposed in 1982 in U.S. Pat. No. 4,360,774 replaces spring-biased buttons with non-depressable buttons. The intent of all these improvements was to equalize the contact areas of ten discrete electrodes thereby increase the repeatability.

One great benefit of Franklin tester is that it does account for degradation in surface resistivity due to the clamping pressure and temperature during operation. Surface resistivity of an isolated lamination free of clamping pressure can range from 1 to 200 ohm $cm^2$ depending on the coating thickness. Clamping pressures can reduce it by nearly 50%. Operating temperatures further degrade it. Under combined stacking pressures and temperatures, coating can soften and become thinner, further reducing the surface resistivity. These effects are satisfactorily accounted for by the Franklin tester.

But even after equalizing the contact area and accounting for pressure and temperature effects, Franklin Tester still suffers from several limitations. One fundamental limitation is that it does not test the entire surface and hence is unable to detect shorts that may be present in untested areas of insulation which could lead to catostraphic core failure. Other concerns include, but not limited to, not accounting for variations in surface resistivity from one location to another, limited ability to apply sufficiently large voltage typical in large machines, and lacking provisions to follow crowned profile of laminations. These limitations resulted in Franklin tester's inability to distinguish between good quality insulation that can prevent core failure and bad quality insulation that can cause core failures, thereby rising questions about its usefulness. This created a demand for an improved test apparatus and test method that more accurately depects the quality of insulation which can prevent core failures.

That Franklin tester does not account for variations in surface resistivity can be seen from the following rationale. Surface resistivity is the product of the coating's electrical resistivity and thickness. While resistivity is a material property and hence is a constant, the thickness of the coating is not constant and varies from point to point. FIG. 2-B shows a zoomed view at location M of the coating 4. This mangified view shows that the coating thickness is non-uniform, and varies widely from point to point, from a maximum thickness $t_{max}$ to a minimum thickness $t_{min}$. It is not unusual for coating thickness to vary by 50% to 90% or even 100%. In fact Marion-Pera (1994) found few spots with no coating, that is, iron shows on a coated surface in microscopic spots that are not seen by naked eye. Thus surface resistivity can vary by 50% or more depending on the location, and Franklin tester does not do a good job of accounting for this large variation, and it does not detect microscopic spots where there is no insulation and hence can cause electrical shorts.

That Franklin tester does not apply sufficient voltage stress on the surface insulation can be seen from the following rationale. The standard dictates that it should apply a relatively low voltage of 0.5 volts across coating. While this low voltage suffices for testing small or medium sized machines, it may be too low to test the surface insulation in lamination used in large machines. Large generators operate at very high voltage and power levels (voltage>20 kV, power>500 MW). Laminations in such high voltage machines are subjected to relatively high interlaminar voltages at core ends. At core-ends, interlaminar voltage may be 40 or 50 times higher than those in main body of the core (Anderson et al 1980) in steady state. During transient conditions, they may be two or three times higher. In fact, at the core-end, one generator manufacturer measured steady interlaminar voltage of ~5 v peak-to-peak (Platt 1982). Another manufacturer estimated that, at the core end, steady interlaminar voltage will be more than 1V. In contrast, the Franklin tester applies only 0.5 V across laminations. Hence the voltage applied by Franklin tester is significantly lower and inadequate to test laminations of large generators. As a result, the core ends of such large machines are extremely vulnerable to failure by electrical shorts or bad quality insulation that is not detected by the Franklin tester.

That Franklin tester does not follow crowned profile of laminations can be seen from following rationale. It is well known that laminations are not uniformly thick; this nonuniformity is characterized by crown and edge drop, as described in U.S. Pat. No. 7,004,002. Crown refers to a gradual reduction in thickness as one moves from the width center towards edges of steel strip. For example, a 0.35 mm (0.014 inch) thick steel strip typically has crown of about 5 μm (200 pinch). This means that surface of lamination is not perfectly flat at any point, and is microscopically slanted. As a result, even if all contact buttons are perfectly flat, since the lamination surface is slanted, buttons do not completely touch the insulated surface. This mismatch in flatness leads to different buttons contacting with different areas, thereby resulting in scatter in test results.

That Franklin tester does not test a large area of surface insulation can be seen from FIG. 2-A. This shows a representative lamination 1 used in utility generators; it has a large area of back iron and a smaller area containing teeth. The total insulated area can be as high as 1300 $cm^2$ (200 $in^2$). Also shown is tested area 7 comprising ten discrete imprints 90 under ten discrete electrodes 91. Per ASTM standard A717-06, the total tested area 7 is 6.54 $cm^2$ (1 $in^2$). The balance area 9 is 1293 $cm^2$ (200−1=199 $in^2$) or 99.5% of insulated surface remains untested. The prior art attempted to overcome this untested area problem by repeating the Franklin test over 5 to 10 different areas and take an average. But ten tests only increase the tested area to about 10 $in^2$, which still leaves 190 $in^2$ or 95% of the insulated area untested.

Perhaps the most fundamental and serious limitation of Franklin tester is its inability to detect defective spots within the insulative coating that can create electrical shorts. Defective areas are localized microscopic spots where resistance of surface insulation is zero or near zero. These defective spots are so small and microscopic that they cannot be seen by naked eye. As already explained, more than 95% of the coated area is not tested. This large untested area 9 could contain single or plurality of defective spots 92, 93, 94. They may occur either on the surface, on the edge of a lamination or on a tooth corner where the act of punching leaves an elevated surface and coating could be chipped away in a microscopic spot. These surface insulation defects are very difficult to detect by naked eye, but they could cause havoc on the performance of the machine. Such surface insulation defects could be caused by wide and varied sources, such as conductive debris, lumps on surface, bared spots, thin coating, pin holes, embedded conductive particles, burrs, rised edges, bared insulation at tooth corners etc.

If the insulated surface has a defect, then eddy current freely travels from one lamination to next. Shorting of two laminations effectively doubles lamination thickness so quadruples the eddy current. Shorting of three laminations increases eddy currents by a factor of 9. Such sharp amplification of eddy currents in confined and localized areas leads to concentrated heat; as this concentrated heat cannot be dissipated in confined areas, it leads to hot spots. Local temperature of such hot spots is builds up to such high value that at some point it burns the coating, melts the iron and welds the laminations. Surface insulation defects hence can lead to devastating core failure.

Published literature on generator core failures summarised below indicates that one major cause is interlaminar shorts caused by defects in the insulation coating. In 1968, in a power plant operated by CEGB (currently National Grid) Britain, a 500 MW generator core was damaged by melting per Fairney (1989). In a simulation of this 500 MW generator, Tavner and Anderson (2005) predicted that currents as high as 11,500 Arms could circulate due to an interlaminar short. In 1998, a 300 MW generator in San Antanio, Tex., overheated because of numerous interlaminar shorts and was removed from service leading to economic losses per Spisak (2004). In 2000, core failure occurred in a 415 MW generator in Castle Dale, Utah, in which about 200 pounds of molten iron flowed out from the end of the stator core, the cause for which was traced to a small interlaminar short which grew into a major melt zone per Edmonds et al (2007).

Thus even though the surface insulation in areas exposed to Franklin tester's contact buttons has high surface resistivity—as seen by low or near zero Franklin currents—defects in the surface insulation could lead to core failure. From this discussion, it is apparent that even if a lamination passes Franklin tester, it does not necessarily mean that a defective surface insulation protects the machine from core failure. Because of inadequacy of Franklin tester to detect defective insulation, there is a strong need for an surface insulation tester that could detect the failure-prone defects within the insulation coating and reject bad quality laminations. This invention described herein aims to fill this need, thereby reducing chance of core failure and resulting outages and economic loss. The present invention is not restricted to measuring surface resistivity. It can also measure other characteristics of an insulative coating, such as number of defects per unit area, dielectric strength etc.

SUMMARY OF THE INVENTION

Accordingly, several objects and advantages of the present invention are:

to provide an apparatus that identifies a specific punching or steel strip that contains defective insulation, facilitating their rejection, thereby reducing the possibility of core failure.

to provide an apparatus that could prevent core failure that can be integrated into a coating line in a steel mill or electrical machinery manufacturing plant.

to provide an improvement over a Franklin Tester by testing entire coated surface instead of testing a small area.

to measure other metrics of quality of insulation of coatings on the electrical steel, such as surface resistivity, number of defects per square inch, breakdown voltage etc.

The proposed invention employs continuous movement of a conductive cylindrical surface over the entire coated surface of a test specimen comprising a base metal coated with an thin insulative coating. The method includes electrically conductive cylindrical surface engaged with an insulative material on a conductive sheet material for movement there between. The invention uses cylindrical electrode (instead of discrete button electrodes) that roves (instead of being stationary) over the entire surface of insulation (instead of testing a small area of insulation). The roving tester can be implemented in a variety of embodiments, the variations depending on whether the cylindrical electrode is hard or soft, whether one or two sides of the coating are tested, or whether test is conducted in single or multiple passes etc. The cylindrical electrode is said to be soft if its hardness is an order of magnitude lower than that of the coating 4. The cylindrical electrode is said to be hard if its hardness is an order of magnitude higher than that of the coating 4. The hardness greatly affects the contact area and hence the contact pressure. Further objects and advantages of the invention will become apparent from consideration of the drawings and ensuring description.

BRIEF DESCRIPTION OF THE DRAWINGS

FIG. 1 is a schematic of the prior art Franklin tester.

FIG. 2-A shows the area in a specimen that is not tested by a Franklin tester.

FIG. 2-B show zoomed view showing variations in thickness of coating.

FIG. 3 shows a preferred embodiment 100 of the invention that employs a soft cylindrical electrode.

FIG. 4-A shows an alternative embodiment 200 of the invention that employs a hard cylindrical electrode.

FIG. 4-B shows an alternative embodiment 300 of the invention for testing insulation both sides.

FIG. 5 shows a roving means for moving the tester over the surface of test specimen.

FIG. 8-A shows an electrical connection diagram that is used to conduct the surface insulation tests.

FIG. 8-B shows an electrical circuit schematic indicating various electrical resistances in the path of electric current.

FIG. 9 shows method of roving the cylindrical electrode over the test specimen.

DESCRIPTION OF THE EXEMPLARY EMBODIMENTS

Figure 6:
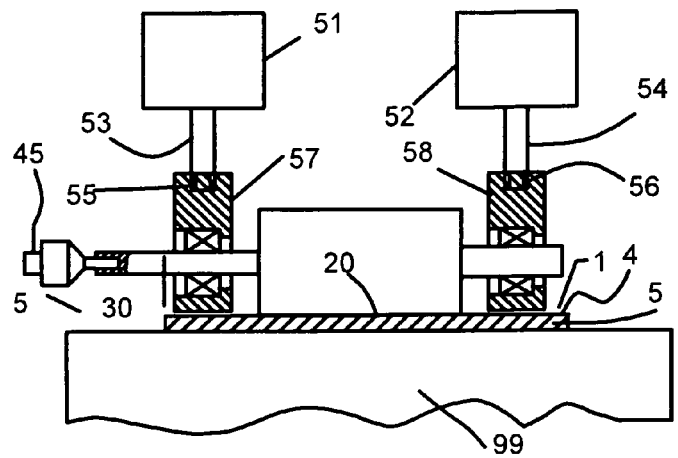
FIG. 6 shows an external pressure means using dead weights for applying specified contact pressure.

FIG. 3 shows a schematic of a preferred embodiment 100 of the present invention, termed a roving tester. During test, the roving tester 100 sits on top of a test specimen 1 which itself is attached to a work table 99. The roving tester 100 comprises a nonrotatable spindle 131 and a rotatable cylindrical electrode 135 mounted on the same axis of rotation. A stationary electrical terminal 133 is drilled into the non-rotatable spindle 131. A cylindrical electrode 135 is mounted rotatably and symmetrically over the spindle 131 using a pair of bearings 138 and a pair of flanges 134, all located on same axis of rotation. Cylindrical electrode 135 is a tube that is compressible, soft and is electrically conductive. Its inner surface is initially stretched and then slipped to fit snugly over a cylindrical surface 141 of the pair of flanges 134. Inner race of the bearing 138 is nonrotating and mated with the nonrotatable spindle 131, while outer race of the bearing 138 is rotatable and is mated with the rotatable flange 134. A narrow annulus is formed by the inner surface 143 of the flange 134 and the hub 142 of spindle 131. A pool of liquid metal 136 is trapped in this narrow annulus.

The purpose of liquid metal 136 is to facilitate flow of current with very low resistance from nonrotatable spindle 131 to the rotatable cylindrical electrode 135. This pool of liquid metal 136 can be mercury. This pool of liquid metal 136 is sealed using multiple seals. As a minimum, one pair of liquid seals 137 is mounted between a groove 142 on the outer surface of the hub of the spindle 131 and the inner surface 143 of the flange 134. Optionally, two pairs of seals 140, 139 within the bearing 138 between its inner and outer races, another pair of seals 150 between the outer pheriphery of spindle 131 and inner periphery of flange 134 seal the liquid metal. These plurality of seals prevent any leakage of liquid metal. Both inner surface 143 and hub 142 are molecularly bonded to mercury to minimize electrical resistance. During testing, when the cylindrical electrode 135 rotates, electrical current conducts from it into the inner surface 143 of the rotating flange 134. Pool of liquid metal 136 then conducts current through shearing of liquid between rotating and nonrotating surfaces. The current flows from power supply into nonrotatable terminal 133 and then into rotatable cylindrical electrode 135 via conduction path 172 as shown. Elements within the conduction path 172, such as flange 134, pool of liquid metal 136, non-rotatable shaft 131 are sized to ensure that the resistance of the conduction path is substantially lower than that of the insulation layer 4, by one or two orders of magnitude.

The purpose of cylindrical electrode 135 is to provide a rotating electrical contact with coated surface 4 at specified pressure and temperature. Before assembly, the cylindrical electrode 135 looks like a collapsed rubber tubing that is relatively soft compared to the hard coated surface 4. The inner diameter of cylindrical electrode 135 before assembly is slightly smaller than the outer diameter of flange 134. To assemble, this cylindrical electrode tubing is stretched and fitted over outer periphery of flange 134. The length of cylindrical electrode 135 is chosen to be slightly larger than maximum width of the test specimen 1 so that test can be completed in one pass to minimize the time of testing. Alternatively length of cylindrical electrode 135 can be a fractional multiple of width of test specimen which enables the test to be performed in more than one pass. The shore hardness of the cylindrical electrode 135 could range from A55 to A70. The shore hardness is chosen so that the roving tester 100 applies a specified contact pressure on the insulative coating 4 under the self weight of roving tester 100. The surface finish of the cylindrical electrode 135 is chosen to be high enough to reduce the rolling resistance between it and insulation layer 4. Cylindrical electrode's 135 volume resistivity and wall thickness are chosen so that its surface resistivity is two to four orders of magnitude lower than lowest resistivity expected from the coating surface 4. This will ensure that the measurement of the surface resistivity of coating 4 is not corrupted by that of the roving tester. Cylindrical electrode 135 can be made of commercially available conductive elastomers or conductive plastics which have the capability of continuous operation at a temperature specified for the test. The material is chosen so that it can be inexpensively replaced if it is damaged by electrical shorts or carbonization. Cylindrical electrode 135 can alternatively made of harder material without altering the invention.

During testing, the cylindrical electrode 135 is pressed against a test specimen due to gravitational force, i.e., dead weight of tester 100. Since cylindrical electrode 135 is softer than test specimen, it gets compressed under gravity, deforms locally at the interface 20 between cylindrical electrode 135 and the coated surface 4, and takes a substantially flattened position. The size of the contact area in the flattened position depends mainly on the hardness of cylindrical electrode 135 and the tension at which cylindrical electrode 135 stretched and assembled. A simple method to estimate contact pressure p is to measure the dead weight W and contact area A. The average contact pressure is then calculated from p=W/A. Diameter and shore hardness of cylindrical electrode 135 are adjusted to achieve the required contact pressure. The contact pressure can also be measured by sandwiching a pressure film (not shown) between the tester and coated surface. Commercially available pressure films indicate the contact pressure by changing the color depending on the pressure. Note that contact pressure inside the contact area can vary from location to location, depending on geometry of cylindrical electrode 135, with maximum contact pressure occurring at the center of contact area, and smallest pressure occurring near edge. These pressure variations are minimized by choosing the proper geometry and materials.

FIG. 4-A shows the schematic of an alternative embodiment 200 of the roving tester. This roving tester 200 comprises a cylindrical electrode 10, shafts 12a, 12b and a rotatable electrical connector (abbreviated as REC) 30, all located on the same axis of rotation. FIG. 4-A also shows the roving tester 200 resting on top of a test specimen 1. The test specimen 1 itself is attached to a flat worktable 99. The cylindrical electrode's round surface 13 makes a line contact 20 with the coating's surface 4. (in FIG. 4-A this line contact is shown as one line 20 for the sake of clarity). An electric circuit 38 applies a specified voltage across the terminal of REC 45 and a drill bit contact 43 electrically connected to the base metal 5 of the test specimen.

In the roving tester 200, cylindrical electrode 10 is preferably harder than that of test specimen 1, but it can be made softer without altering the invention. The round surface 13 of cylindrical electrode 10 is conductive and has its ends 13a, 13b attached to a conductive shaft 12a, 12b. The cylindrical electrode 10 and shafts 12a, 12b can be individual parts that are assembled on the same axis of rotation, or integrated into a single member with synchronised axis of rotation. The construction ensures that the current passes from the surface of shaft 12a to the round surface 13 of cylindrical electrode 10 with least resistance.

During test, the round surface 13 of cylindrical electrode 10 and insulation coating 4 meet at contact interface 20. Since the round surface 13 is harder than the coating 4, the coating 4 deforms locally at interface 20. The contact area will be relatively small, and hence the contact pressure will be relatively high. Different electric machines use different pressures to clamp the core, so the hardness of cylindrical electrode 10 can be tailored to meet the requirements of specific machines, or it can be set at a prescribed standard pressure. The round surface 13 of cylindrical electrode 10 is highly polished, with mirror-like surface finish, and is free of any blemishes. The cylindrical electrode's 10 hardness, flatness, surface finish, roundness, runout, cylindricity are precisely controlled to ensure that its surface 13 contacts with the coated surface 4 without any air gap.

In the embodiment 200, a commercial Rotatable Electrical Connector 30 is attached concentrically to shaft 12a. A primary function of REC is to make a low-resistance electrical contact between a rotatable shaft 12a and a nonrotatable electrical terminal 45. FIG. 4-A schematically shows a key detail of a Rotatable Electrical Connector. Rotatable Electrical Connector 30 has, on one end, a stationary electrical terminal 45 to which a regulated power supply 38 is connected. On the other end, it has a knurled shaft 41 that is press-fitted into a blind hole in the shaft 12a. Internally, Rotatable Electrical Connector 30 also has a pool of mercury (not shown) that is molecularly bonded to the rotatable and nonrotatable parts so as to provide a low-resistance electrical path. When the shaft 12a the liquid metal transfers current between rotatable and nonrotatable parts at low resistance without any wear. The resistance of commercially available REC that employ mercury is less than 1 milliohm while that of insulation (without defects) is greater than 20 milliohm, so insulation tests are not affected by the resistance of REC 30. Several firms such as Mercotac, Carlsbad, Calif. manufacture the RECs. Other types of REC that employ devices such as slip rings and brushes have resistance significantly more than 1 mohm, so are not preferred.

The shaft 12b is sized such that its weight equals that of shaft 12a plus REC 30. This ensures that the center of gravity of the electrode 10, shafts 12a, 12b plus REC 30 coincides with that of the electrode 10 alone.

Cylindrical electrode 10 is sized so that, when placed over the test specimen 1, the total weight of cylindrical electrode 10, shafts 12a, 12b and rotatable electrical connector 30 exerts on the test specimen 1 a contact pressure that equals the required test pressure.

For tests using Roving tester 200 to be accurate, the contact resistance at the round surface/coating interface 20 plus that of REC 30 must be significantly smaller than the resistance of the insulation across coating 4. So special care must be taken in manufacturing cylindrical electrode 10 to ensure that the contact resistance at interface 20 is as small as possible. Cylindrical electrode 10 should be ground flat and polished to ensure that there is no air gap between it and the coating 4. Any external load on the tester 200 must be uniformly distributed any resulting bending deflection will not create air gap at interface 20.

FIG. 4-B shows an alternative embodiment 300 of roving tester which tests insulation on both sides 4a, 4b of steel strip or a lamination. This roving tester 300 is suitable for use with a coating line. After coating is applied on both sides of steel strip and fully cured, the steel strip or lamination 1 passes between two rollers 25, 26 under pressure. The rollers rotate in opposite directions. These rollers are conductive and are in full mechanical and electrical contact with the cured coating 4a, 4b on both sides of strip 1. Rotatable electrical connectors 37, 38 are attached to the rollers 25, 26 at one end. To test the insulation quality of coating, a regulated power supply 24 is connected to stationary terminals of rotatable electrical connectors as shown and it applies a regulated voltage. Current then passes from supply 24 into REC 37, into roller 25, into coating 4a on first side of steel strip 1, then into iron 5, into coating 4b on second side of stell strip 1, into roller 26 back to complete the circuit through REC 38. A plotter 39 attached to a current sensor continuously monitors the current flowing through the coating. If the coating is of high quality insulation, then current flowing through it will be low and will not drastically change over time. If there is a defect in the coating on any side, large current will flow and the current plot will show an abrupt peak.

FIG. 5 shows a simple roving means to rove the cylindrical electrode 10 parallel to the coating surface 4. This specific roving means comprises a fork-shaped handle 15 attached to housings 57, 58. Bearings 14a, 14b are mounted on shafts 12a, 12b and they support cylindrical electrode 10 symmetrically and are contained in a nonconductive housings 57, 58. Housings 57, 58 have two cylindrical recesses 46, 47 in which bearings 14a, 14b are fitted. The handle 15 consists of a U-shaped connector 16 (whose ends are attached to the housings 57, 58), a long stem 17 (that is attached to connector 16), and a hand grip 18 (that is attached to stem). One can alternatively integrate handgrip 18, stem 17, connector 16 and housing 57, 58 into a single member. When external means are used to apply pressure, bearings 12a, 12b ensure that only cylindrical electrode 10 and shaft 12a, 12b roll over the test specimen while all other parts are stationary. A person skilled in the art can envision alternate means to rove, such as a pulley and belt attached to a drive motor without altering the invention.

Figure 7:
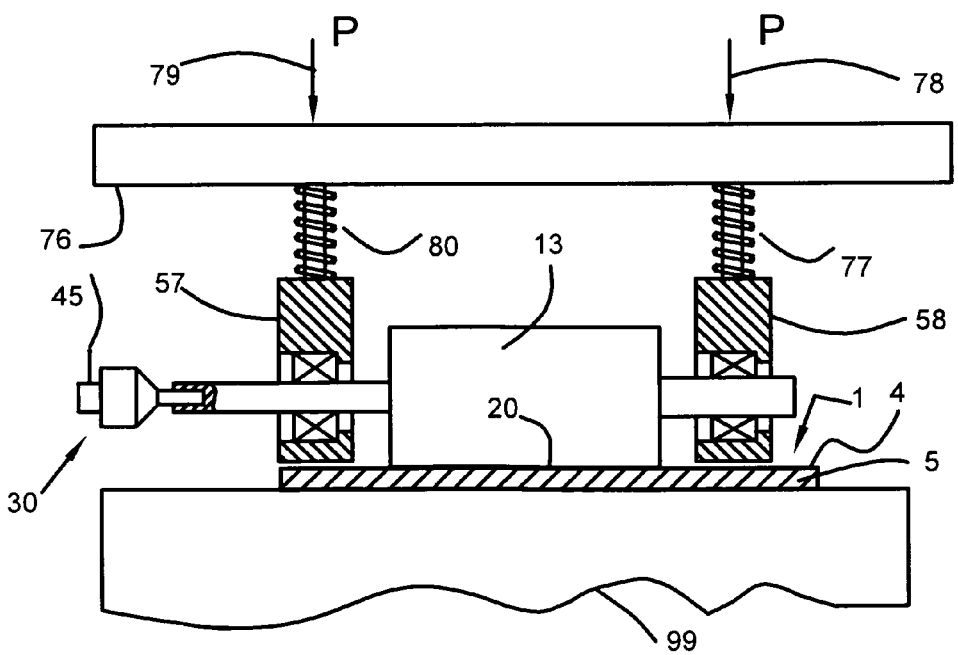
FIG. 7 shows an alternative external pressure means using pumps to apply specified contact pressure.

FIGS. 6 and 7 illustrate two means of applying specified pressure on the coating using external devices. FIG. 5 already shows a simple method which involves pressing a handle 15 down by hand while roving; but this method results in non-uniform pressure. FIG. 6 shows an alternative pressure means using dead weight blocks. Known weight blocks 51a, 51b are screwed into the housing 57, 58 using rods 53, 54 that have threaded ends 55, 56. Housing 57, 58 have blind threaded holes that accept these thread rods. Weight blocks 51a, 51b are equal in weight and their total weight determines contact pressure. By changing the blocks, an operator can increase or decrease the contact pressure. FIG. 7 shows an alternative means that uses pumps to apply contact pressure. An external pump (not shown) applies a force at 78, 79 on load plate 76, and the hydraulic load is transmitted to cylindrical electrode 10 via springs 77, 80. Springs 77, 80 are attached to housing 57, 58 and load plate 76. As in the Franklin tester, a person skilled in the art would select the alignment means needed to ensure that the applied force and contact pressures are aligned and do not create tilting forces. Although two external pressure means are shown, it must be understood that a person skilled in the art can conceive of alternative means to apply pressure without altering the basic invention.

FIG. 8-A shows an electrical connection schematic that can be used to test the insulation quality of coating 4 using the roving tester 100. The circuit consists of a regulated power supply 31 that applies a predetermined voltage across the coating 4. A voltmeter 34 is connected across the terminals of the power supply 31 to monitor the applied voltage. One output terminal of the power supply 31 is connected to one terminal 45 of the spindle 131, while other is connected to a drill bit terminal 44 that bites into the base metal 5 of test specimen 1. An external resistor R in the circuit is adjusted to normalize current to 1 Amp when test specimen is a conductive flat plate. A current sensor 102 in the current path measures the current that flows through the coating. The output signal from current sensor 35 is fed into a plotter 101 to make a current vs. time plot.

FIG. 8-B displays an electric circuit diagram that shows key resistances in the path of current. When the power supply 31 is energized, the conduction path is 172 as shown, and current flows into REC 45, through its mercury contact into cylindrical electrode 135, through contact interface into coating 4, into the base metal 5 to complete the circuit. The circuit has four major resistances—an external resistor R, internal resistance of REC $R_{REC}$, contact interface's contact resistance $R_{CR}$, and resistance of coating $R_{COAT}$. The resistance of REC $R_{REC}$ and contact resistance $R_{CR}$ should be much smaller than that of the coating $R_{COAT}$. The electrical connection diagram shown in FIG. 8-A and circuit diagram shown in FIG. 8-B correspond to soft roving tester 100 shown in FIG. 3. They can be easily adapted to the hard roving tester 200 shown in FIG. 4-A by a person skilled in the art without altering the invention.

FIG. 9 describes a method of roving the roving tester 100 or 200 to test the entire coated surface. An operator starts from a first end 108 with cylindrical electrode covering the entire surface of test specimen 1. He then rolls the roving tester 100 or 200 along path 115 towards the second end 103 in a single pass. Alternatively, multiple passes can be used to rove the roving tester by using a cylindrical electrode that is half the width of test specimen. Alternative embodiments of roving means, such as using electric motors to pull the cylindrical electrode, can be visualized without altering the invention.

Roving testers 100, 200, 300 shown in FIG. 3 and/or FIG. 4-A, 4-B can be used in several ways to measure the insulation quality of a coating. Specifically described below are methods to use it to measure the surface resistivity, to detect a defective insulation, to measure the dielectric strength of a coating, to correct insulation defects, to record insulation quality, or to measure other metrics such as insulation defects per square inch. Test specimen 1 is laid flat on a work table 99. Appropriate roving means to rove the roving tester, such as that shown in FIG. 5, is chosen. Appropriate external pressure means to apply required contact pressure (such as self weight, external weights or pumps as shown in FIG. 6, 7) are attached to the cylindrical electrode 10. Regulated power supply 31, ammeter 102, voltmeter 34, resistor 36, plotter 101 etc. are connected both to terminal 45 of REC and to a drill bit connection 44 to the base metal as shown in FIG. 8-A. To calibrate, roving tester 100 or 200 is placed over a flat conductive plate and roved over its entire insulation surface. The resistor R is adjusted such that the ammeter reads 1 A at all times. During this roving operation, a plotter continuously plot current vs. time history. A reading of near-zero amps at any point indicates that the coating is of high insulation quality. A reading of nearly 1 amp at any time indicates a defective test specimen.

Figure 10:
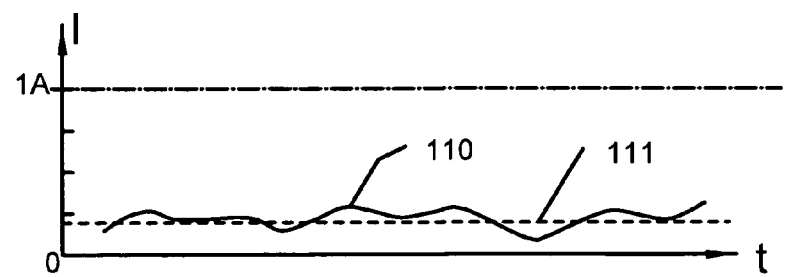
FIG. 10 shows a current plot that results in estimation of surface resistivity of the coating.

FIG. 10 shows a current vs. time plot 110 when a roving tester is used to measure the surface resistivity of a coating. To achieve this, test specimen 1 is placed on work table 99 and roving tester 100 or 200 is roved under specified contact pressure and temperature. This plot 110 indicates that average value 111 of current across the coating is very small, less than 0.25 amps. Absence of any sharp spikes in the current plot indicates that this coating is free of insulation defects. Surface resistivity can then calculated from measured value of current as done in the ASTM standard.

Figure 11:
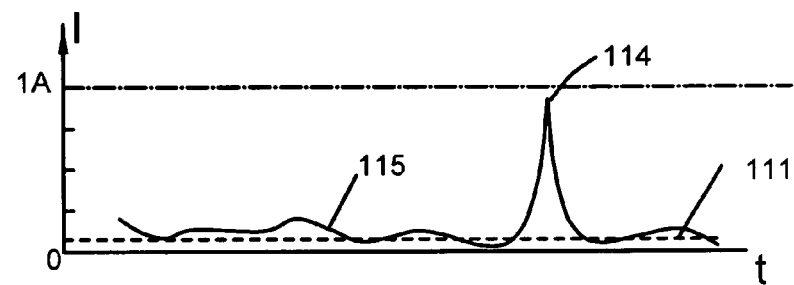
FIG. 11 shows a current plot that can be used to detect defects in the coated surfaces.

FIG. 11 shows a current vs. time plot when a roving tester is used to detect defects in an insulative coating. The test specimen 1 is placed on a work bench 99 and cylindrical electrode 10 is roved as already described. Suppose that the current plot 115 shows that very small current leaks through coating's surface most of the time as it is roved. But, at one location, suppose it shows a sharp current spike 114. A spike corresponds to a spot with defective insulation. Note that this plot shows that the average current 111 is relatively low. This is because the sharp spike in current does not significantly affect the value of average current. If one were to use average current as a metric for the insulation quality, one could wrongly conclude that surface resistivity of the coating 4 is relatively high, so the coating protects the machine against core failure. But this figure shows that even when the surface resistivity is high, the insulation can have a defect at which two successive laminations can short. At this location, test specimen has zero or near zero resistance, which could allow large eddy currents to flow from one lamination to another. This could eventually lead to core failure as already described.

Figure 12:
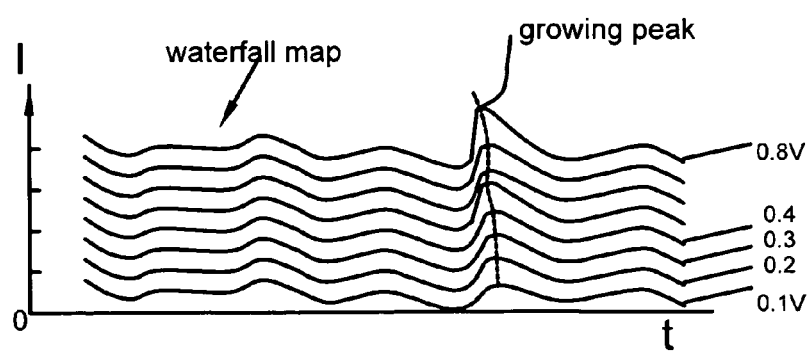
FIG. 12 shows a waterfall map of current vs. time data that can be used to define the dielectric strength of a coating.

FIG. 12 shows a water fall map that can be used to determine dielectric strength of a thin coating. Dielectric strength is a voltage gradient (expressed in volt/mil, under specific conditions of test) at which a dielectric coating fails—i.e., there is evidence of a sharp decrease in resistance. To estimate this, one can conduct a test as described in the ASTM standard D149, but modify it by using the following waterfall map. To start the test, a power supply is set to apply a specific minimum test voltage $V_{min}$ of say 0.1 volt. A roving test is carried at prescribed contact pressure and specified speed of rolling. Resulting current vs. time data is plotted as a first curve labeled 0.1V in a waterfall plot shown in FIG. 12. The test voltage is then increased by a prescribed increment $\Delta V$ of say 0.1 V to 0.2 volt. Roving test is repeated, and resulting current vs. time data is plotted as a second curve labeled 0.2V in a waterfall plot; this curve is positioned slightly above a first curve. The process is repeated. This builds up a water fall plot. An agreed breakdown criterion is then established. This could be an irreversible phenomenon such as an abrupt, visible and/or audible rupture through the coating, a visible puncture, a shorted black spot, discoloration, decomposition of coating, or a prescribed value of leakage current etc. A breakdown voltage is determined from the waterfall map using this criterion. For example, if breakdown voltage is defined as that at which 0.8 amps of electric current flows through the coating, the voltage needed to attain this value can be read from the waterfall map. The roving tester has the ability to detect defects in the coating and reject laminations with bad quality coatings. Or it can be used to reinsulate locally at the defective spot through a feedback control system thereby restoring the insulation quality. Alternatively, the current plot can be used as a record of the insulation quality of the coating on the steel strip or lamination. In small and medium machines, it is possible that one is likely to accept presence of limited number of defects in the insulation, with the hope that a specified number of defects do not cause a catastrophic failure. In such cases, the roving tester can be used to measure number of defects per unit area, and this can be used as a go/no go metric of quality of coating.

From preceding description, it is apparent that the roving tester described herein has several advantages over the traditional Franklin tester. In testing the roving tester is roved over the entire coating surface which means that no part of coating is left untested. The roving tester can be used to measure surface resistivity just as a Franklin tester does, but it also can be used to detect defects or measure dielectric strength of a coating, which Franklin tester cannot do. The Roving tester provides a current history plot which records continuously the insulation effectiveness of the coating compared to the Franklin tester. Use of cylindrical electrode 10 instead of flat contact buttons also reduces wear and increases the life of the tester. Spikes in current plot can locate spots of defective insulation while the mean value can capture the average surface resistively. The roving tester thus improves repeatability of results. In short, roving tester can determine if the coating has good insulation characteristics that protect a machine against core failure or bad quality insulation that could trigger a core failure.

What is claimed is:

1. An apparatus for testing the quality of an electrical steel lamination, said lamination having a first end and a second end and having a first coating on a first surface and a second coating on a second surface, comprising:
   a) a stationary cylindrical spindle having an axis of rotation and a stationary electrical terminal,
   b) a rotatable cylindrical member having an electrically conductive compressible surface and concentrically mounted about said spindle axis,
   c) an integral sealed annulus containing liquid metal built into said rotatable cylindrical member to electrically connect said rotatable cylindrical member and said stationary electrical terminal,
   d) the length of said rotatable cylindrical member longer than the width of said electrical steel lamination, and
   e) the diameter of said rotatable cylindrical member and hence dead weight of said apparatus sized to apply a specified compressive pressure over said first coating on the electrical steel lamination.

2. A method for testing the quality of an electrical steel lamination employing the apparatus in claim 1, comprising:
   a) positioning said apparatus in claim 1 centrally over said electrical steel lamination, with said conductive surface of said rotatable cylindrical member in electrical and mechanical contact with the first coating of said electrical steel lamination,
   b) exploiting the dead-weight of said apparatus in claim 1 to apply a specified compressive pressure over the first coating on the said electrical steel lamination,
   c) applying electric current between said stationary electrical terminal and the electrical steel,
   d) defining a reciprocating cycle comprising moving the apparatus in claim 1 over said electrical steel lamination in one direction from the first end of said electrical steel lamination to the second end of said electrical steel lamination, reversing direction and moving back from the second end of said electrical steel lamination to the first end of said electrical steel lamination,
   e) repeating said reciprocating cycle for a specified number of times, and
   f) detecting the quality of said electrical steel lamination by counting the current spikes and averaging the amount of electric current.

* * * * *